United States Patent [19]

Ellison et al.

[11] Patent Number: Plant 5,549

[45] Date of Patent: Sep. 3, 1985

[54] ASPARAGUS PLANT

[75] Inventors: J. Howard Ellison, Milltown; John J. Kinelski, Princeton, both of N.J.

[73] Assignee: Rutgers University, New Brunswick, N.J.

[21] Appl. No.: 539,156

[22] Filed: Oct. 5, 1983

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A male asparagus plant which is homogenetic and transmits particularly the characteristics of male genes and which include high yield capability, resistance to rust (*Puccinia asparagi*), tolerance to root rot (*Fusarium oxysporum*) and crown rot (*F. moniliforme*), enabling production of male hybrids that likewise embody such characteristics.

2 Drawing Figures

We have long conducted an intricate and exhaustive program of development of asparagus, some of the prime objectives thereof being to reduce or eliminate the effects of diseases, provide substantially increased productivity with both size and volume of produced spears being sought.

Since asparagus does in fact transmit many of these attributes through the male plant, much effort has been directed to producing and seeking male plants that do in fact have characteristics which result in attaining the ends sought, selection of desirable male plants having resulted in the invention hereof as a particular example.

This program has been and is being conducted in the vicinity of New Brunswick, N.J., in both fields and greenhouses, certain prior plants having been developed which meet the objectives, but as is always the case continually seeking to improve being also desirable as in fact resulted in a number of improvements in the asparagus art of which this is a good example.

The instant variety, a male denominated originally as No. 22-8, is now to be known as "Scott Howard", and is a homogenetic, first selfed generation seedling, and was produced by self fertilization of an andromonoecious male which we identify in our records as No. 22 U.S. Plant Pat. No. 4,999 and found to transmit only male genes, resulting in production of progeny in turn which are all male hybrids.

A desirable resistance to rust (*Puccinia asparagi*) and tolerance to root rot (*Fusarium oxysporum*) and crown rot (*F. moniliforme*) which the male plant hereof in turn offers for its progeny, makes the variety hereof useful for crossing with suitable female plants to in turn produce hybrids which are commercially useful.

It is well known that transmission of male sex expression is valuable because male plants yield more and live longer than females, and this is borne out by the detailed programs which we have followed and of which we have maintained detailed records for comparison and selection.

Figure 2:
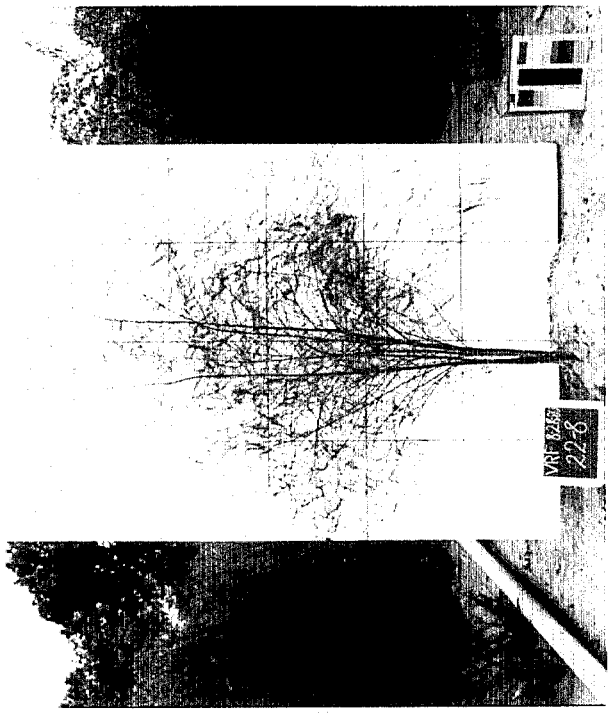
Figure 1:
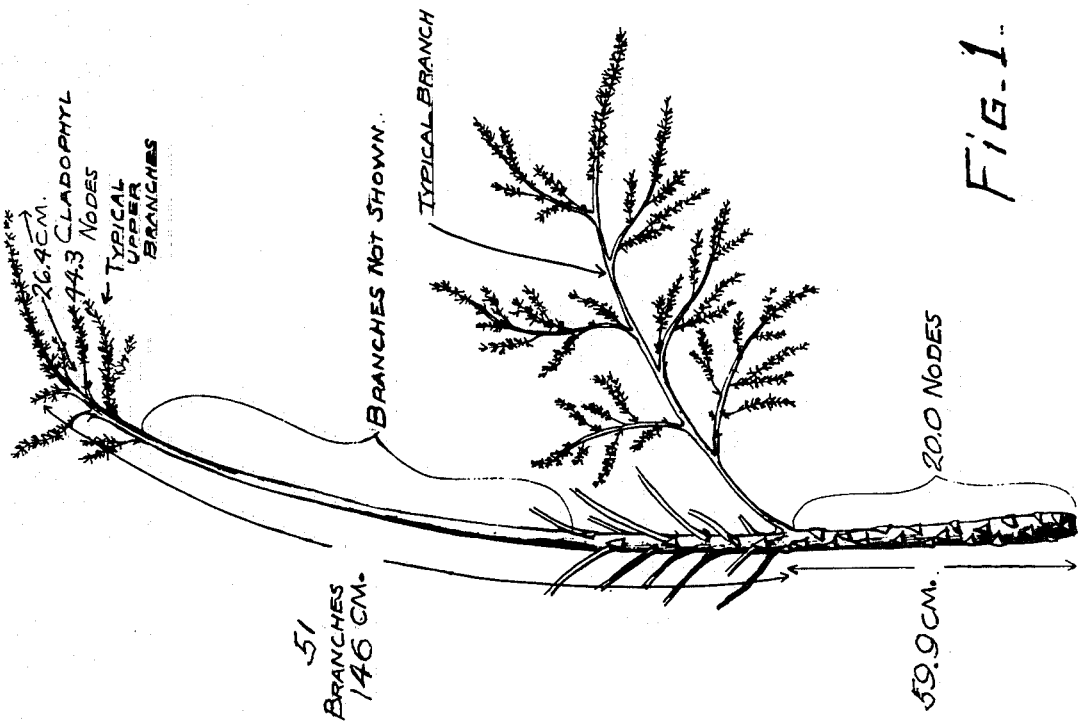

Included in the records maintained by us, is the data hereinafter noted, from which it will be observed that there are in fact a number of aspects which support the validity of our selection. dr In order to illustrate some of the distinguishing features of our new variety we have provided the accompanying drawing which shows in FIG. 1 in black and white with notations applied, a stalk of a typical plant, and in FIG. 2 an entire plant by a color illustration with color as nearly representative as it is possible to make the same in a photograph of the kind supplied, color notations derived therefrom referring to the Munsell Limit Color Cascade.

It is obvious that the colors observed are influenced by the density of growth and subject to different interpretation depending upon the eye of the observer.

| | |
|---|---|
| Stalk Data | |
| Number of nodes below first branch | 20.0 |
| Number of cm from crown to first branch | 59.9 |
| Number of branches | 51 |
| Number of cm between first and last branch | 146 |
| Internode length in cm between branches | 2.86 |
| Number of cladophyll nodes beyond last branch | 44.3 |
| Number of cm beyond last branch | 26.4 |
| Internode length in cm beyond last branch | 0.60 |
| Largest stalk diameter in mm | 17.4 |
| Mean diameter of three largest stalks in mm | 16.0 |
| Number of stalks | 31 |
| Stalk vigor index (No. X Mean diam.$^2$) | 7,936 |
| Mature stalk color, bloom removed | 22–14.1 |
| Flower Data | |
| Petal tip (yellow) | 24–5 |
| Petal base (brown) | 35–15 |
| Flower length in mm | 7.12 |
| Flower width at midpoint in mm | 2.80 |
| Cladophyll Data | |
| Number per node | 5.0 |
| Length (mm) | 12.61 |
| Width (mm) | 0.130 |

(1) Color number. Munsell Limit Color Cascade. Munsell Color. Macbeth Color and Photometry Division, 2441 Calvert Street, Baltimore, Maryland 21218

We anticipate that this male plant No. 22-8, "Scott Howard" will be used in many instances as a male parent in crosses which will be made as it has already been used in producing certain varieties we have previously developed.

We have asexually reproduced our new variety No. 22-8 "Scott Howard" by crown division and tissue culture and find that it comes true in successive generations.

We claim:

1. A new and distinct variety of Asparagus Plant as herein shown and described, distinguished particularly as to novelty by its unique combination as a homogenetic first selfed generation male seedling produced by self fertilization of an andromonoecious male, which transmits only male genes, and which in turn transmits particularly the quality of high yield, resistance to rust (*Puccinia asparagi*), tolerance to root rot (*Fusarium oxysporum*) and crown rot (*F. moniliforme*) and thereby facilitates growth of male hybrids to replace standard cultivars which are susceptible to disease.

* * * * *